United States Patent [19]

Goe et al.

[11] Patent Number: 5,149,816
[45] Date of Patent: Sep. 22, 1992

[54] HIGH TEMPERATURE PROCESS FOR SELECTIVE PRODUCTION OF 3-METHYLPYRIDINE

[75] Inventors: Gerald L. Goe, Greenwood; Robert D. Davis, Indianapolis, both of Ind.

[73] Assignee: Reilly Industries, Indianapolis, Ind.

[21] PCT Appl. No.: Jul 7, 1989

[86] PCT. No.: PCT/US89/02969
 § 371 Date: Apr. 1, 1991
 § 102(e) Date: Apr. 1, 1991

[87] PCT Pub. No.: WO90/00546
 PCT Pub. Date: Jan. 25, 1990

[22] Filed: Jan. 4, 1991

Related U.S. Application Data

[63] Continuation-in-part of Ser. No. 217,686, Jul. 11, 1988, abandoned.

[51] Int. Cl.$^5$ ............................................. C07D 213/09
[52] U.S. Cl. ........................................ 546/251; 546/252
[58] Field of Search ................................ 546/251, 252

[56] References Cited

U.S. PATENT DOCUMENTS

| | | | |
|---|---|---|---|
| 2,790,804 | 4/1957 | Parker | 546/251 |
| 3,225,083 | 12/1965 | Clare | 546/251 |
| 3,542,847 | 11/1970 | Drinkard et al. | 546/251 |
| 3,551,474 | 12/1970 | Drinkard et al. | 546/251 |
| 3,562,311 | 2/1971 | McClure | 546/251 |
| 3,903,079 | 9/1975 | Heinz et al. | 546/251 |
| 4,086,237 | 4/1978 | Daum et al. | 546/251 |
| 4,179,576 | 12/1979 | Miyake et al. | 546/251 |
| 4,401,189 | 8/1983 | Cordier et al. | 546/251 |
| 4,422,981 | 12/1983 | Omori et al. | 546/251 |
| 4,523,016 | 6/1985 | Grigoleit et al. | 546/251 |

FOREIGN PATENT DOCUMENTS

| | | | |
|---|---|---|---|
| 579146 | 6/1933 | Fed. Rep. of Germany | 546/251 |
| 7005792 | 10/1971 | Netherlands | 546/251 |
| 755534 | 8/1956 | United Kingdom | 546/251 |
| 1164354 | 9/1969 | United Kingdom | 546/251 |
| 1488355 | 10/1977 | United Kingdom | 546/251 |
| 2165844 | 4/1986 | United Kingdom | 546/251 |

OTHER PUBLICATIONS

The Merck Index: 10th Ed.; p. 377 (1983).
The Merck Index 9th Ed.; p. 1274 (1976).
Adkins, Reactions of Hydrogen, 1937, University of Wisconsin, pp. 11-14.
Thomas, Catalytic Processes and Proven Catalysts, Academic Press, 1970 pp. 11-14.
Kirk-Othermer Encyclopedia of Chemical Technology, 3rd Ed., vol. 15 pp. 899-909.
I. G. Farbenind, "Heterocyclic Compounds,", *Chemical Abstracts*, vol. 27 (1933) p. 4539.
I. G. Farbenind, "Heterocyclic Compounds", Chemical Abstracts, vol. 27 (1933). p. 4541.
I. G. Farbenind, "Heterocyclic Compounds", *Chemical Abstracts*, vol. 27 (1933) p. 4239.
J. L. Hales and E. F. G. Herington, "Equilibrium Between Pyridine and Piperidine", *Faraday Society, London, Transactions, London*, vol. 53 (1957) pp. 616-622.
N. I. Shuikin and V. B. Brusnikina, "Catalytic Conversions of Piperidine in a Hydrogen Atmosphere", *Zhur. Boshchei Khim, vol. 29 (1959) pp. 434-441*.
J. Sonnemans, J. M. Janus and P. Mars, "Surface Structure and Catalytic Activity of a Reduced Molybdenum Oxide-Alumina Catalyst. 2. The Mechanism of Pyridine Hydrogenation and Piperidine Dehydrogenation", The Journal of Physical Chemistry, vol. 80, No. 19 (1976) pp. 2107-2110.

*Primary Examiner*—M. Cintins
*Assistant Examiner*—John Peabody
*Attorney, Agent, or Firm*—Woodard, Emhardt, Naughton Moriarty & McNett

[57] ABSTRACT

A process for the selective production of 3-methylpyridine in high yield comprising the step of contacting a vaporized feed stream containing 2-methyl-1,5-pentanediamine with a metal-oxide catalyst of other than an alkali metal at a temperature of about 500°-600° C. for a contact time of less than about 30 seconds. The catalyst may be on a suitable heterogeneous support, and additives in the feed stream may include 3-methylpiperidine as well as water, hydrogen, ammonia, or nitrogen or some other inert gas. A fluid-bed reactor is preferred, with recycling of by-product and continuous effective runs without catalyst regeneration being accomplished at the stated temperatures.

29 Claims, No Drawings

HIGH TEMPERATURE PROCESS FOR SELECTIVE PRODUCTION OF 3-METHYLPYRIDINE

REFERENCE TO RELATED APPLICATIONS

This is a continuation-in-part application of pending U.S. patent application Ser. No. 217,686, filed Jul. 11, 1988 and now abandoned.

BACKGROUND OF THE INVENTION

The object of this invention is to provide a new, economical process for the selective production at high yield of 3-methylpyridine (also called beta-picoline) through the catalytic cyclization of a pentanediamine derivative, namely 2-methyl-1,5-pentanediamine. Another object is the similar conversion of a mixture of this acyclic compound and a piperidine derivative, namely 3-methylpiperidine (also called beta-pipecoline), to the same desired 3-methylpyridine product.

As background, the value of this invention is enhanced by the fact that the starting materials are readily available often as by-products from the manufacture of other large-volume products. For instance, in the manufacture of adiponitrile which is an important intermediate in making nylon, the addition of hydrogen cyanide to butadiene also gives 2-methylglutaronitrile (MGN) as a by-product in large quantities. Kirk-Othmer, *Encyclopedia of Chemical Technology*, Third Edition, Vol. 15, p. 899; U.S. Pat. Nos. 3,542,847 and 3,551,474. Hydrogenation of this MGN can then provide 2-methyl-1,5-pentanediamine (MPDA) as a major product.

For example, British Patent No. 1,488,335 issued in 1977 to Dynamit Nobel describes MGN hydrogenation in the prior art to mostly 2-methyl-1,5-pentanediamine (MPDA) and some 3-methylpiperidine, while examples in the '335 patent describe reversed product ratios as its invention. U.S. Pat. No. 2,790,804 issued in 1957 to ICI and British Patent No. 2,165,844 issued in 1986 to ICI similarly describe hydrogenation of unsubstituted glutaronitrile to pentanediamine and piperidine. MPDA can also be conveniently prepared by hydrogenation of 2-methyleneglutaronitrile, which is a product of the dimerization of acrylonitrile. British Patent No. 1,164,354 issued in 1969 to Toyo Rayon; U.S. Pat. No. 3,225,083 issued in 1965 to Shell; U.S. Pat. No. 3,562,311 issued in 1971 to Shell; and U.S. Pat. No. 4,422,981 issued in 1983 to Mitsubishi.

Pyridine derivatives, on the other hand, are known to be useful for many purposes. For example, pyridine is valuable as a solvent and as an intermediate for agricultural chemicals. 3-Methylpyridine (beta-picoline) is itself useful as a solvent and as an intermediate for the manufacture of nicotinic acid and nicotinamide, both forms of the pellagra-preventative vitamin. Goe, "Pyridine and Pyridine Derivatives", Kirk-Othmer, *Encyclopedia of Chemical Technology*, Third Edition, Vol. 19.

In the past, cyclization and dehydrogenation reactions known to produce pyridine and its derivatives have been comprehensively reviewed originally by Brody and Ruby in Volume 1 of *Pyridine and Its Derivatives*, E. Klingsberg, ed., and most recently by Bailey, Goe and Scriven, in Vol. 5 of the *Supplement to Pyridine and Its Derivatives*, G. C. Newkome, ed. These reactions have generally been carried out in the gas phase at low to moderate temperatures up to about 400° C. and for various times using predominantly precious metal catalysts such as palladium and platinum. For example, British Patent No. 755,534 issued in 1956 to ICI describes the conversion of pentanediamine (PDA) to pyridine in 55% yield using a catalyst of 5% platinum on a silica support at 400° C. This document also reports the conversion of PDA to piperidine using acidic heterogeneous catalysts such as silica, silica-alumina beads and boron phosphate, without the precious metal or any other metal component at 350° C. Other examples include the following:

Netherlands patent application No. 7,005,792 (Deumens, Groen, and Lipsch, 1971 to Stamicarbon; Chem. Abstr., 76, 46099) reports converting PDA to piperidine in high yield using a catalyst of Raney-nickel supported on silica or to various mixtures of piperidine and pyridine using a catalyst of palladium supported on alumina at 125°–300° C.

U.S. Pat. No. 4,086,237 issued in 1978 to Dynamit Nobel (equivalent to German Patent No. 2,519,529) reports the conversion of MPDA alone or with 3-methylpiperidine to mostly 3-methylpyridine using palladium metal on an alumina support at 200°–400° C. U.S. Pat. No. 4,401,819 issued in 1983 to Rhone-Poulenc reports a similar conversion using a precious metal on a particular macroporous solid silica support at 200°–500° C. However, no examples are given at the upper end of this temperature range, and preferred temperatures are reported to be 250°–400° C.

British patent application No. 2,165,844 filed in 1986 by ICI reports the eventual conversion of glutaronitrile to pyridine, perhaps with the preferred isolation of 1,5-pentanediamine as an intermediate, using palladium metal on silica support at 350°–400° C.

Collectively, these references show that pentanediamine and its alkyl derivatives have been selectively converted in the past to their piperidine counterparts using catalyst supports alone or in combination with the Group VIII nickel metal, or to admixtures of these piperidines and their pyridine counterparts using various Group VIII precious metals (also called noble metals) including palladium and platinum at moderate temperatures of about 400° C. This work has suffered from the disadvantage that only these precious metal catalysts have been shown to selectively produce acceptably-high yields of the pyridine compounds such as 3-methylpyridine. Besides their high initial cost, these expensive precious metal catalysts pose added handling problems and cannot be economically used in fluid-bed reactors (which are advantageous for many reasons including their temperature uniformity and ease of catalyst regeneration) because of the catalyst losses that inevitably occur in such processes.

Thus, there has been a growing need and economic driving force for a process useful for the selective conversion of pentanediamine derivatives (such as 2-methyl-1,5-pentanediamine) to their pyridine counterparts (such as 3-methylpyridine) in high yields using effective and readily available catalysts that are inexpensive, that are susceptible of regeneration, and that most preferably can be operated in fluid-bed reactors. The applicants' pending U.S. patent application Ser. No. 217,686, filed Jul. 11, 1988 and entitled PROCESS FOR SELECTIVE PRODUCTION OF 3-METHYLPYRIDINE describes additional work by the applicants to date to meet these needs. In particular, this prior application describes a process for the selective production of 3-methylpyridine in high yield using preferred transition metal-oxide catalysts of copper chromium or molybdenum. These preferred catalysts are inexpensive as compared to the Group VIII precious metal catalysts of the prior art while performing comparably thereto at temperatures predominantly used in the prior art, namely, about 400° C.

Nevertheless, there remains a need for a process for the selective production of 3-methylpyridine which is not critically limited to select few, and often expensive catalysts as in the case of precious metals. The applicants, through their continued work in this field, have made a surprising and significant discovery which meets this need.

SUMMARY OF THE INVENTION

In particular, the applicants have discovered a high temperature process for the selective production of 3-methylpyridine directly from 2-methyl-1,5-pentanediamine (MPDA) alone or admixed with 3-methylpiperidine, as in the hydrogenation products of 2-methylglutaronitrile (MGN). This process comprises the step of contacting a vaporized feed stream containing at least the acyclic MPDA compound with a metal-oxide catalyst of other than an alkali metal, at a temperature of about 500°-600° C. for a time of less than about 30 seconds. These temperatures are significantly higher than any taught to be acceptable for these reactions in the prior art, and provide significant improvement over prior art lower temperature processes which are effective only when a select few catalysts are used in these reactions.

One embodiment of this process utilizes a fluid-bed reactor for efficiency and ease of operation including separation and recovery of the condensed 3-methylpyridine product and recycling of any 3-methylpiperidine that may be present. In other embodiments, oxides of copper chromium, molybdenum and vanadium are the catalysts of choice either unsupported or on a suitable heterogeneous support such as silica, alumina or a combination thereof as in an amorphous or a crystalline zeolite form. In the case of copper chromites, also preferred has been the presence of barium or manganese in its oxide form. In the case of vanadium oxides, it has also been preferred that zinc oxide be present. Possible additives to the feed stream include water, hydrogen, ammonia, and nitrogen or other inert gases.

The applicants have also discovered that at the high temperatures of about 500°-600° C., additional advantages of significantly-extended catalyst life and activity have been experienced with their preferred and other catalysts without the need for as frequent regeneration. Contact times of about 10 seconds or less have also shown to be preferred, which lessen the chance of product decomposition at these elevated temperatures while maintaining high levels of conversion and yield of the desired 3-methylpyridine product.

Related objects and advantages of the present invention will be apparent from the following description.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such alterations and further modifications in the invention and such further applications of the principles of the invention as described herein being contemplated as would normally occur to one skilled in the art to which the invention relates.

As stated above, the applicants have discovered that a pentanediamine derivative, preferably 2-methyl-1,5-pentanediamine (MPDA), is readily and selectively converted to its pyridine counterpart, preferably 3-methylpyridine, when contacted with catalysts made of metal-oxides other than alkali metal-oxides. This contacting step (and resulting reaction) takes place at a temperature of about 500°-600° C. and for a time of less than about 30 seconds.

The applicants' effective catalysts have included both supported and unsupported forms. It is appreciated, however, that catalysts supported on a suitable low-cost heterogeneous support such as silica, alumina or silica-alumina in some form can be an economic advantage particularly in a fluid-bed operation. Indeed, the applicants' have demonstrated that at the high temperatures of their invention, silica, alumina, and silica-alumina themselves are effective catalysts for the selective production of 3-methylpyridine.

The most effective and preferred catalysts to date have comprised oxides of copper chromium (particularly copper chromites unsupported and promoted with barium or manganese in oxide form) and molybdenum and vanadium oxides (on a variety of supports).

In this regard, the applicants' use of the term "copper-chromium" defines a class of metal-oxide catalysts containing copper and chromium which may be present in varied valence states and have been subjected to a reducing atmosphere in the presence of hydrogen or other reactants pursuant to one of many different procedures. This term, and these catalysts and their preparations, have long been known in the art as, for example, discussed in the 1937 book by Homer Adkins entitled *Reactions of Hydrogen with Organic Compounds over Copper-Chromium Oxide and Nickel Catalysts* (and particularly pages 11-14) which is incorporated herein by reference as to all matters relevant and material to this application. Similarly, the term "copper chromite" is of more contemporary vintage and defines the class of catalysts comprising copper and chromium in various oxide forms after being calcined according to standard and known procedures. Several copper chromites are commercially available, for example, as identified in the specific Examples below.

The applicants' use of the term "effective" relates to the catalyst's ability to selectively produce the desired 3-methylpyridine product in high yields under the reaction steps and conditions as defined herein. Various of the experimental results achieved by the applicants to date are set forth in the specific Examples and Tables below. However, in view of the number of variables present, an "effective" or "high" yield of 3-methylpyridine under these circumstances constitutes one that is commercially significant. This is preferably one that approaches a net yield of about 40% or more 3-methylpyridine based on a conversion approaching 100% of the original organic feed stream. Alternatively, it is also preferred that by-products be limited principally to 3-methylpiperidine in a comparative yield of about 1:2 or less relative to the 3-methylpyridine produced. In this regard, it is particularly preferred that 3-methylpiperidine be present in a comparative yield of about 1:3 or less relative to the 3-methylpyridine produced. This 3-methylpiperidine can then be recycled back through the feed stream to make more of the desired pyridine product.

Methods for the preparation of the applicants' catalysts are well known in the art. The preferred method to data in the case of an unsupported catalyst has been for the metal salt to be precipitated and then decomposed to the desired oxide by heat. For a supported catalyst, a salt that is soluble in water, such as ammonium molybdate or various nitrates, has been first absorbed on the desired support and then decomposed to the desired oxide by heat (also known as calcining). An alternative method is to form the desired metal oxide as an ion-exchanged form of a zeolite, and then to calcine the resulting zeolite salt to form the desired catalyst. These and other methods known to those of ordinary skill in this art can be used in preparing the catalysts of the applicants' processes. Suitable catalysts are also commercially available as in the case of an unsupported copper chromite material marketed by The Harshaw/Filtrol Partnership (now Engelhard Corporation) of Cleveland, Ohio. Regardless of their source, however, these catalysts can be prepared or purchased in many usable sizes and shapes such as pellets, extrusions or spheres for fixed-bed use or as powders or microspheroidal materials for fluid-bed use. These and other physical factors involved in catalyst selection, preparation and handling vary with the specific equipment, conditions and reaction selected, and are well within the ordinary skill of those in this field.

The applicants' reactions have been preferably carried out in the usual fashion of continuous gas-phase reactions of this type, in which the reactants are vaporized and this feed stream then passed in contact with the catalyst which is maintained at the desired temperature. In this way, the vaporized reactants are conducted over the catalyst to produce a suitable contact time for the reaction to take place. This contact time may be seen as the time required to achieve a desired or maximum conversion which is often expressed as a percentage of the original reactants passed. The preferred contact time in a particular reaction must be found by trial and error under the specific circumstances involved, unless prior comparative data is available.

The applicants have found that contact times of about 30 seconds or less are preferred in their work to date. Contact times of about 10 seconds or less have proven even more desirable. In fact, experiments have shown that minimizing the contact time is preferred and that conversions approaching 100% of the reactants used and net yields of 3-methylpyridine approaching about 40% or more of these conversions have still been achieved. Significantly longer contact times may require specially designed equipment, and can result in product decomposition or other unwanted by-products at the elevated temperatures involved.

For example, the applicants' reactions carried out at temperatures in the range from about 500°–600° C. have maximized the conversions achieved with a preference to the desired 3-methylpyridine product for the wide variety of metal-oxide catalyst materials set forth in the specific Examples and Tables below. A temperature of about 550° C. has been preferred to data for maximizing conversion and for other advantages discussed below. In this regard, each reaction must be examined on its own to determine optimum conditions, including temperature, under given circumstances.

The applicants' reactions have proven suitable for fixed-bed or fluid-bed operation. Fixed-bed reactors in this field are well documented both in practice and in the literature. The same is true of fluid-bed reactors, although more variables exist. For example, the feed rates of the vapor reactants are chosen to give sufficient fluidization of the catalyst bed. These are usually at a superficial velocity between about 0.25 ft/sec (0.08 m/sec) and 3.0 ft/sec (0.9 m/sec), although lower or higher velocities may be chosen in given circumstances. The reaction products are then collected by condensation and individual products are separated and recovered as desired, frequently by distillation means. As noted below, if the process yields a mixture of the piperidine and pyridine derivatives, one alternative is to subject the mixture to further catalytic reaction to dehydrogenate the remaining piperidine material. Another alternative is to first isolate the pyridine product and then to recycle only the piperidine component back through the reactor. In any case, the general construction and operation of a fluid-bed or a fixed-bed reactor are no different for the applicants' processes than for other reactions for which they are used. Reference can thus be made to available literature or other sources in this area as to the specific establishment and operation of such reactors, the same being well within the skill of those practiced in this art.

As for the starting materials used, the applicants' preferred feed stream needs only to contain an amount of 2-methyl-1,5-pentanediamine (MPDA) as a reactant for the process. This acyclic compound is vaporized and passed in contact with the heated catalyst bed to bring about the reaction. Other materials may also be present in the feed stream as long as they do not interfere significantly with the selective production of 3-methylpyridine in high yields as previously described.

For example, since pentanediamines have been known to cyclize producing a mixture of pyridine and piperidine derivatives under prior art conditions, one alternative has been the inclusion of the corresponding 3-methylpiperidine compound in the feedstock without detracting from the advantages achieved with the applicants' preferred processes. The 3-methylpiperidine present has simply dehydrogenated thereby producing even more of the desired 3-methylpyridine product. Since pentanediamines have been produced by hydrogenation of a dinitrile such as 2-methylglutaronitrile (MGN), which is also known to produce cyclized compounds such as piperidines as by-products, a useful feedstock for the applicants' reactions has been a mixture of the pentanediamine and piperidine derivatives produced by the hydrogenation of this MGN material. Separation of these MGN hydrogenation products as feed components has been unnecessary under these circumstances, which is a substantial time and cost savings over many prior art processes in this area.

Additional materials have proven suitable for inclusion in the applicants' reaction feed stream as well. One such additive has been hydrogen, which when used has shown some advatage in a molar ratio of about 1:1 or more hydrogen to organic in the feed stream. Since hydrogen is not consumed, but rather generated in the reaction, it is advantageous in a commercial application to recycle this hydrogen. It may also be possible to obtain hydrogen initially as a by-product of some other process in the plant.

A second possible additive has been water which may be supplied in the form of steam. This additive has been used with some advantage in experiments to date in a molar ratio of about 5:1 or more water to organic in the feed stream. It should be recognized, however, that any water remaining in the product mixture must be later separated out and that the failure to account for this water can reflect as a lower material balance for the reaction. Evidence of this is found in the Tables below.

Still other possible additives have included nitrogen (or other inert gases) and ammonia. Nitrogen has been used as a diluent or carrier gas particularly in reactions with small amounts of organic component in the feed stream. Ammonia has been used in other experiments, both additives being in molar ratios of about 5:1 or more to the organic component. Since ammonia is a reaction product similar to hydrogen, however, it must be recovered in any commercial application and possibly purged for use elsewhere or destroyed.

A recognized problem with catalysts in this area has been that their activities gradually decrease over time. With most catalysts regeneration is possible, for example, by heating in the presence of air or some other oxygen-containing gas. See Charles L. Thomas, *Catalytic Processes and Proven Catalysts*, pp. 11–14 (1970). This may be followed by passing hydrogen over the hot catalyst before returning it to contact with a further reactant stream. This need for periodic regeneration encourages the use of fluid beds for such reactions, which beds are capable of being regenerated either in total at certain intervals or in part by the catalyst being continuously or intermittently circulated to a second reaction vessel in which regeneration takes place. Such reactors are commonly used in industry for reactions such as the catalytic cracking of petroleum and in pyridine synthesis.

Another aspect of the applicants' invention has been the discovery that their preferred catalysts have been able to retain acceptable activity levels for significantly longer times than are common in this art. This has occurred at temperatures in the range of about 500°–600° C., with about 550° C. being preferred to date. This is substantially above any temperature known to have been taught or suggested in the art as being acceptable for this type of reaction. While quantitative analysis in this area is difficult, the applicants have found that repeated runs with their preferred catalysts at these temperatures have shown fairly constant and acceptable conversions and yields without intervening regeneration. This is a significant advantage in catalyst life and in the elimination of the downtime normally involved in regeneration.

While the invention has been described in detail in the foregoing paragraphs, the same is to be considered as illustrative and not restrictive in character. It is understood that only the preferred embodiments have been described and that all changes and modifications that come within the spirit of the invention are desired to be protected.

In this regard, some specific Examples and Tables follow which reflect experimental runs performed by the applicants using their catalysts and processes described above. In these, reference is made to 2-methyl-1,5-pentanediamine as "MPDA," to 3-methylpiperidine as "MePip" and to 3-methylpyridine as "Beta." "Conversion" is expressed as a percentage calculated by dividing moles of organic compound reacted by moles of organic compound fed into the reactor in the feed stream. "Gross yield" is expressed as a percentage calculated by dividing moles of specific product obtained by moles of organic compound fed into the reactor in the feed stream. "Net yield" is expressed as a percentage calculated by dividing moles of product obtained by moles of organic compound reacted. "Contact times" for the reactions were all in the range of about 4–10 seconds, unless otherwise specified, and minimal superficial velocities ("Sup. Vel.") were observed to maintain fluidization of the catalyst bed. Examples 1–35 were generally low-temperature runs, whereas Examples 1A–35A were generally high-temperature runs using the same catalysts as the low-temperature runs. For instance, Example 1 details a run using a copper chromite catalyst at 395° C., whereas Example 1A uses the same catalyst at higher temperatures of 497° to about 550° C. Similar catalyst correspondence is found throughout Examples 1–35 and 1A–35A.

In all but Example 37, a fluid-bed reactor was used. This reactor consisted of a 1.6-inch (4.1-cm) ID × 5-foot (1.5-m) 316 stainless steel pipe with a gas furnace covering the lower 3 feet (0.9 meters) and a 5-inch (13-cm) ID disengaging bell equipped with a filter at the top. The catalyst charge was generally 750 ml and the catalyst particles were of a size suitable for fluidization, generally in the range of about 20–850 micrometers (or microns). The key in this regard is to be able to fluidize the particle bed, and the equipment used will often dictate the preferred particle size for this purpose. In this regard, the feed vaporizer used was an electrically heated 0.75 inch (1.9-cm) × 26-inch (66-cm) stainless steel pipe. Vaporized feed was introduced into the bed by means of a perforated tube sprayer. Gases were preheated by passage through an electrically heated 0.25-inch (0.64-cm) × 20-inch (51-cm) stainless steel pipe. Preheated gases were introduced into the bed by means of a distributor plate.

EXAMPLE 1

80 g of MPDA/hour and 95 g of water/hour were fed from a calibrated blowpot into the fluid-bed reactor containing 625 ml (1107 g) of Harshaw copper chromite catalyst (#Cu-1107T, containing 33% CuO, 37% $Cr_2O_3$ and 7% BaO as listed active components). The MPDA used was obtained commercially under the trademark "DYTEK-A" marketed by the E. I. duPont de Nemours & Company, and was used in all the Examples below unless otherwise specified. The catalyst was originally in tablet form, and had been crushed to pass through 20-mesh (850-micrometer) screen. The feed was vaporized and heated to 360° C. At the same time, 500 L of hydrogen/hour (mole ratio $H_2$/MPDA=30) were heated to 160° C. and passed into the reactor. The reactor temperature was maintained at 395° C. The product was collected by condensation in a 6-foot (1.8-m) water cooled condensor followed by a coil of tubing submerged in ice water. The combined product from the first 30-minute run was analyzed by gas chromatography, showing 100% conversion with 17% net yield of MePip and 80% net yield of Beta which was a significantly high result even compared to prior art processes using expensive precious metal catalysts. The combined product from the second 30-minute run showed 100% conversion with 43% net yield of Beta which was still acceptably high. However, the net yield of MePip increased to 51% showing catalyst deactivation as is common and reported in the art at the temperature of this reaction. The MePip from each run was retained and recycled in later feed streams to produce more of the desired Beta product.

EXAMPLE 1A

The reaction was carried out as in Example 1 using a reaction temperature of 497° C., a $H_2$/MPDA mole ratio of 8 and a $H_2O$/MPDA mole ratio of 6.4. The Sup. Vel. was 1.4 (0.43 m/sec). This resulted in 100% conversion with 9% net yield of MePip and 75% yield of Beta in a 30 minute run. In another experiment, consecutive and continuous runs at about 550° C. using the same batch of catalyst (again Harshaw copper-chromite catalyst #Cu-1107T) evidenced the improved selective production of Beta achieved over extended periods at the higher temperatures of the invention without the need for catalyst regeneration. The results are shown in Table 1 below, in which runs (i) and (ii) were 30 minutes long and runs (iii)–(vii) were each 60 minutes long.

EXAMPLE 2A(ii)

The reaction was carried out as in Example 2A(i) using 525 ml (358 g) of the same $MoO_3$ on silica-alumina catalyst at a reaction temperature of 553° C. Thereafter, consecutive runs of 216 g of MPDA/hour, 216 g of water/hour and 210 L of nitrogen/hour (mole ratio $N_2$/MPDA = 5) resulted in 0.1% net yield of MePip and 73% net yield of Beta in the first-hour run, 0.5% net yield of MePip and 99% net yield of Beta in the second hour, 0.7% net yield of MePip and 86% net yield of Beta in the third hour, 1.4% net yield of MePip and 81% net yield of Beta in the fourth hour, and 1.6% net yield of MePip and 81% net yield of Beta in the fifth hour. Conversions were 100% throughout the runs. These significantly selective and high yields of Beta

TABLE 1

| Example | Catalyst[a] | Temp. (°C.) | Additives[b] $N_2$ | $H_2$ | $NH_3$ | $H_2O$ | Sup. V. (ft/sec) | Sup. V. (m/sec) | v. (%) | Net Yield (%) MePip | Beta | Mat. Bal. (%) |
| --- | --- | --- | --- | --- | --- | --- | --- | --- | --- | --- | --- | --- |
| 1A(i) | 33% CuO-37% $Cr_2O_3$-7% BaO | 549 | 5 | 0 | 0 | 6.4 | 1.0 | 0.30 | 95 | 3 | 70 | 96 |
| 1A(ii) | (same as 1A(i)) | 548 | 5 | 0 | 0 | 6.4 | 1.0 | 0.30 | 90 | 5 | 47 | 83 |
| 1A(iii) | (same as 1A(i)) | 545 | 4 | 0 | 0 | 6.4 | 1.1 | 0.34 | 85 | 13 | 45 | 87 |
| 1A(iv) | (same as 1A(i)) | 550 | 5 | 0 | 0 | 6.4 | 1.0 | 0.30 | 91 | 18 | 41 | 86 |
| 1A(v) | (same as 1A(i)) | 552 | 5 | 0 | 0 | 6.4 | 1.0 | 0.30 | 93 | 23 | 41 | 84 |
| 1A(vi) | (same as 1A(i)) | 550 | 4 | 0 | 0 | 6.4 | 1.1 | 0.34 | 89 | 34 | 45 | 84 |
| 1A(vii) | (same as 1A(i)) | 551 | 5 | 0 | 0 | 6.4 | 1.1 | 0.34 | 89 | 35 | 40 | 84 |

[a]Percentages were by weight of total catalyst used as prepared or commercially obtained.
[b]Expressed as moles per mole of organic in feed stream.

EXAMPLE 2

The reaction was carried out in the manner of Example 1 using a temperature of 399° C., but the catalyst, prepared by the standard procedure set forth in Example 2A(i) below, was $MoO_3$ on silica (containing 10% $MoO_3$, 78% silica and 12% alumina). The $H_2$/MPDA mole ratio was 5, and the $H_2O$/MPDA mole ratio was 7.2. At a Sup. Vel. of 1.0 ft/sec (0.30 m/sec), a 100% conversion was obtained with 8% net yield of MePip and 43% net yield of Beta over a 30 minute run.

EXAMPLE 2A(i)

The reaction was carried out as in Example 1, but 750 ml (535 g) of $MoO_3$ on silica-alumina (containing 10% $MoO_3$, 78% silica and 12% alumina) was the catalyst, nitrogen was used in place of hydrogen and the reaction temperature was raised to 545° C. The catalyst was prepared by a standard procedure in which 600 g of silica-alumina was impregnated with a 480 mL solution containing 78 g of molybdic acid in concentrated ammonium hydroxide. The catalyst was allowed to dry overnight, and was then calcined at 500° C. Thereafter, 157 g of MPDA/hour, 174 g of water/hour and 209 L of nitrogen/hour (mole ratio $N_2$/MPDA = 6) resulted in 100% conversion with 0.3% net yield of MePip and 97% net yield of Beta in the first 30-minute run and 100% conversion with 0.4% net yield of MePip and 95% net yield of Beta in the second 30 minutes. Both of these results were extremely high and selective yields of Beta and significant improvements over prior art processes.

were achieved without regeneration of the catalyst and with no indication of catalyst deactivation over time as has been common in this area. These superior results were also in contrast to those obtained using the same components, but at a temperature of 400° C. and with hydrogen in place of nitrogen. In those runs the initial net yield of Beta was 34%, but it decreased to 25% by the end of the first hour and no further runs were made as the trend was obvious toward decreasing and unacceptable yields without regeneration. The 73% net yield of Beta over the first hour of this high temperature run also compares favorably with Example 2 above in which a 43% net yield of Beta was observed over 30 minutes at 399° C.

EXAMPLES 3–34 (Low Temperatures, see Table 2) and EXAMPLES 3A–34A (High Temperatures, see Table 3)

The reactions in these Examples were carried out using the equipment and procedures as described previously in Example 1. Table 2 sets forth runs performed at lower temperatures of about 400° C., whereas Table 3 shows runs performed at the high temperatures of the applicants' processes. A comparison of Tables 2 and 3 reveals the dramatic and surprising increase in the selective production of 3-methylpyridine achieved at these higher temperatures with a wide variety of metal-oxide catalysts. In this regard, catalyst components were obtained commercially, and their supported forms prepared where needed using standard impregnation techniques such as described in Example 2A(i). The organic phase of the feed stream in each Example was MPDA ("DYTEK-A" from duPont) alone, except as noted in the Tables.

TABLE 2

| Example | Catalyst[a] | Temp. (°C.) | Additives[b] $N_2$ | $H_2$ | $NH_3$ | $H_2O$ | Sup. V. (ft/sec) | Sup. V. (m/sec) | Conv. (%) | Net Yield (%) MePip | Beta | Mat. Bal. (%) |
| --- | --- | --- | --- | --- | --- | --- | --- | --- | --- | --- | --- | --- |
| 3 | 1.2% PdO on silica | 303 | 0 | 6 | 0 | 7.2 | 0.9 | 0.27 | 100 | 42 | 58 | 81 |
| 4 | 19% $Fe_2MoO_6$ on si—al | 398 | 0 | 6 | 0 | 7.1 | 1.0 | 0.30 | 100 | 31 | 25 | 86 |

TABLE 2-continued

| Example | Catalyst[a] | Temp. (°C.) | Additives[b] N₂ | H₂ | NH₃ | H₂O | Sup. V. (ft/sec) | Sup. V. (m/sec) | Conv. (%) | Net Yield (%) MePip | Beta | Mat. Bal. (%) |
|---|---|---|---|---|---|---|---|---|---|---|---|---|
| 5 | 19% WO₃ on silica | 395 | 0 | 13 | 0 | 0.0 | 1.0 | 0.30 | 98 | 21 | 22 | 57 |
| 6 | 20% Bi₂O₃ on silica | 398 | 0 | 6 | 0 | 7.6 | 1.0 | 0.30 | 83 | 63 | 8 | 95 |
| 7 | 5% CoO-10% MoO₃ si—al | 402 | 0 | 8 | 0 | 6.4 | 1.2 | 0.37 | 100 | 13 | 39 | 88 |
| 8 | 20% Cr₂O₃ on silica | 395 | 0 | 10 | 0 | 6.4 | 1.6 | 0.49 | 83 | 38 | 3 | 88 |
| 9 | 20% CuO on silica | 399 | 0 | 16 | 0 | 6.4 | 1.3 | 0.40 | 99 | 38 | 8 | 67 |
| 10 | 20% Fe₂O₃ on silica | 398 | 0 | 11 | 0 | 6.4 | 1.3 | 0.40 | 95 | 50 | 13 | 84 |
| 11 | 20% CoO on silica | 398 | 0 | 5 | 0 | 7.2 | 1.0 | 0.30 | 100 | 11 | 25 | 81 |
| 12 | 20% La₂O₃ on silica | 400 | 0 | 6 | 0 | 7.2 | 0.9 | 0.27 | 90 | 50 | 7 | 95 |
| 13 | sulfided 5% CoO-10% MoO₃ on si—al | 396 | 0 | 5 | 0 | 5.4 | 0.9 | 0.27 | 100 | 1 | 98 | 85 |
| 14 | 20% Nb₂O₅ on silica | 399 | 0 | 6 | 0 | 7.6 | 1.0 | 0.30 | 100 | 78 | 7 | 95 |
| 15 | 20% PbO on silica | 404 | 0 | 6 | 0 | 7.2 | 1.0 | 0.30 | 79 | 87 | 9 | 100 |
| 16 | 20% Sb₂O₃ on silica | 397 | 0 | 6 | 0 | 7.6 | 1.0 | 0.30 | 100 | 65 | 9 | 86 |
| 17 | 20% ThO₂ on silica | 399 | 0 | 6 | 0 | 7.2 | 0.9 | 0.27 | 97 | 91 | 4 | 96 |
| 18 | 70% silica-30% MgO | 400 | 0 | 5 | 0 | | 1.0 | 0.30 | 100 | 14 | 16 | 90 |
| 19 | 10% Bi₂O₃-10% MoO₃ in Kaolin | 401 | 0 | 7 | 0 | 6.4 | 0.9 | 0.27 | 100 | 34 | 33 | 87 |
| 20 | 7% CoO-13% Cr₂O₃ on silica | 398 | 0 | 5 | 0 | 6.2 | 0.9 | 0.27 | 100 | 53 | 10 | 85 |
| 21 | 10% CuO-10% MnO₂ on silica | 399 | 0 | 5 | 0 | 5.6 | 0.9 | 0.27 | 97 | 35 | 10 | 85 |
| 22 | 7% CuO-13% MoO₃ on silica | 398 | 0 | 6 | 0 | 7.7 | 1.0 | 0.30 | 99 | 29 | 36 | 88 |
| 23 | 5% CuO-15% WO₃ on silica | 398 | 0 | 6 | 0 | 6.2 | 0.9 | 0.27 | 100 | 20 | 32 | 80 |
| 24 | 10% TiO₂ on silica | 398 | 0 | 6 | 0 | 7.6 | 1.0 | 0.30 | 98 | 43 | 17 | 95 |
| 25 | 10% V₂O₅-10% CuO on silica | 399 | 0 | 5 | 0 | 6.2 | 0.9 | 0.27 | 100 | 58 | 46 | 83 |
| 26 | 10% ZnO on silica | 400 | 0 | 9 | 0 | 6.4 | 1.2 | 0.37 | 100 | 57 | 11 | 91 |
| 27 | 12% V₂O₅ on si—al | 398 | 0 | 5 | 0 | 7.6 | 1.0 | 0.30 | 100 | 49 | 13 | 70 |
| 28 | alumina | 399 | 0 | 6 | 0 | 7.2 | 1.0 | 0.30 | 100 | 77 | 10 | 91 |
| 29 | silica | 392 | 0 | 5 | 0 | 7.2 | 1.0 | 0.30 | 69 | 86 | 14 | 98 |
| 30 | silica-alumina (si—al) | 398 | 0 | 6 | 0 | 6.4 | 0.9 | 0.27 | 100 | 41 | 8 | 80 |
| 31 | 20% CdO on silica | 399 | 0 | 6 | 0 | | 1.0 | 0.30 | 94 | 54 | 13 | 98 |
| 32 | 10% MoO₃p-0.5% Cs₂O on silica | 399 | 0 | 6 | 0 | | 1.0 | 0.30 | 100 | 18 | 7 | 95 |
| 33 | 9% V2O5-11% Bi₂O₃ on si—al | 397 | 0 | 11 | 0 | | 0.9 | 0.27 | 100 | 35 | 31 | 89 |
| 34 | 9% V2O5-14% Sb₂O₃ on si—al | 403 | 0 | 7 | 0 | | 1.2 | 0.37 | 100 | 33 | 32 | 96 |
| 35 | 9% V2O5 8% ZnO on si—al | 401 | 0 | 6 | 0 | | 1.3 | 0.40 | 100 | 35 | 20 | 88 |
| 36[c] | 11% CuO-11% Cr₂O₃ on si—al | 406 | 0 | 17 | 0 | 5.9 | 0.6 | 0.18 | 100 | 0 | 40 | 64 |

[a]Percentages were by weight of total catalyst used as prepared or commercially obtained.
[b]Expressed as moles per mole of organic in feed stream.
[c]Organic feeds were 1:1 weight ratios of "DYTEK-A" and commercial 3-methylpiperidine.

TABLE 3

| Example | Catalyst[a] | Temp. (°C.) | Additives[b] N₂ | H₂ | NH₃ | H₂O | Sup. V. (ft/sec) | Sup. V. (m/sec) | Conv. (%) | Net Yield (%) MePip | Beta | Mat. Bal. (%) |
|---|---|---|---|---|---|---|---|---|---|---|---|---|
| 3A | 1.2% PdO on silica | 550 | 5 | 0 | 0 | 6.4 | 1.0 | 0.30 | 100 | 0 | 83 | 83 |
| 4A | 19% Fe₂MoO₆ si—al | 547 | 5 | 0 | 0 | 7.6 | 1.1 | 0.34 | 100 | 1 | 71 | 83 |
| 5A | 19% WO₃ on silica | 551 | 4 | 0 | 0 | 6.4 | 1.0 | 0.30 | 100 | 1 | 79 | 88 |
| 6A | 20% Bi₂O₃ on silica | 549 | 5 | 0 | 0 | 6.2 | 1.0 | 0.30 | 100 | 2 | 80 | 87 |
| 7A | 5% CoO-10% MoO₃ on si—al | 550 | 4 | 0 | 0 | 6.4 | 1.0 | 0.30 | 100 | 0 | 52 | 87 |
| 8A | 20% Cr₂O₃ on silica | 544 | 6 | 0 | 0 | 6.7 | 0.9 | 0.27 | 100 | 4 | 72 | 81 |
| 9A | 20% CuO on silica | 549 | 6 | 0 | 0 | 6.2 | 0.9 | 0.27 | 100 | 3 | 56 | 78 |
| 10A | 20% Fe₂O₃ on silica | 548 | 4 | 0 | 0 | 6.4 | 1.1 | 0.34 | 100 | 5 | 69 | 82 |
| 11A | 20% CoO on silica | 553 | 4 | 0 | 0 | 6.4 | 1.2 | 0.37 | 100 | 4 | 74 | 77 |
| 12A | 20% La₂O₃ on silica | 549 | 5 | 0 | 0 | 6.4 | 1.0 | 0.30 | 100 | 1 | 64 | 70 |
| 13A | sulfided 5% CoO-10% MoO₃ on si—al | 550 | 5 | 0 | 0 | 6.4 | 1.0 | 0.30 | 100 | 0 | 99 | 85 |
| 14A | 20% Nb₂O₅ on silica | 547 | 6 | 0 | 0 | 5.6 | 0.9 | 0.27 | 100 | 2 | 76 | 96 |
| 15A | 20% PbO on silica | 544 | 5 | 0 | 0 | 5.6 | 1.0 | 0.30 | 100 | 6 | 53 | 84 |
| 16A | 20% Sb₂O₃ on silica | 548 | 4 | 0 | 0 | 6.4 | 1.1 | 0.34 | 100 | 3 | 97 | 87 |
| 17A | 20% ThO₂ on silica | 542 | 5 | 0 | 0 | 6.2 | 1.0 | 0.30 | 100 | 17 | 52 | 85 |
| 18A(i) | 70% silica-30% MgO | 557 | 5 | 0 | 0 | | 1.0 | 0.30 | 100 | 0 | 68 | 100 |
| (ii) | 70% silica-30% MgO | 505 | 5 | 0 | 0 | | 1.0 | 0.30 | 100 | 0 | 55 | 79 |
| 19A | 10% Bi₂O₃-10% MoO₃ in Kaolin | 550 | 4 | 0 | 0 | 6.4 | 1.1 | 0.34 | 100 | 3 | 97 | 85 |
| 20A | 7% CoO-13% Cr₂O₃ on silica | 549 | 6 | 0 | 0 | 5.6 | 0.8 | 0.24 | 100 | 7 | 75 | 89 |
| 21A | 10% CuO-10% MnO₂ on silica | 545 | 5 | 0 | 0 | 6.2 | 1.0 | 0.30 | 100 | 24 | 66 | 82 |
| 22A | 7% CuO-13% MoO₃ on silica | 553 | 6 | 0 | 0 | 6.4 | 0.8 | 0.24 | 100 | 3 | 56 | 73 |
| 23A | 5% CuO-15% WO₃ on silica | 544 | 5 | 0 | 0 | 6.2 | 1.0 | 0.30 | 100 | 4 | 81 | 81 |
| 24A | 10% TiO₂ on silica | 561 | 5 | 0 | 0 | 5.4 | 0.9 | 0.27 | 100 | 1 | 74 | 83 |
| 25A | 10% V₂O₅-10% CuO on silica | 547 | 5 | 0 | 0 | 6.2 | 1.0 | 0.30 | 100 | 0 | 100 | 81 |
| 26A | 10% ZnO on silica | 548 | 4 | 0 | 0 | 5.4 | 1.0 | 0.30 | 100 | 1 | 70 | 79 |
| 27A(i) | 12% V₂O₅ on si—al | 548 | 6 | 0 | 0 | 7.6 | 1.0 | 0.30 | 100 | 3 | 87 | 81 |
| (ii) | 12% V₂O₅ on si—al | 497 | 6 | 0 | 0 | 7.6 | 1.1 | 0.34 | 100 | 16 | 75 | 87 |
| 28A | alumina | 550 | 5 | 0 | 0 | 6.4 | 1.0 | 0.30 | 100 | 0 | 48 | 75 |
| 29A | silica | 542 | 5 | 0 | 0 | 6.7 | 1.0 | 0.30 | 100 | 3 | 51 | 79 |
| 30A | silica-alumina (si—al) | 549 | 6 | 0 | 0 | 6.4 | 0.9 | 0.27 | 100 | 0 | 48 | 75 |
| 31A | 20% CdO on silica | 553 | 4 | 0 | 0 | | 1.2 | 0.37 | 100 | 4 | 74 | 77 |
| 32A | MoO₃-0.5% Cs₂O on silicia | 563 | 4 | 0 | 0 | | 1.2 | 0.37 | 100 | 1 | 29 | 87 |
| 33A | 9% V2O5-11% Bi₂O₃ on si—al | 553 | 5 | 0 | 0 | | 1.0 | 0.30 | 100 | 0 | 59 | 77 |
| 34A | 9% V2O5-14% Sb₂O₃ on si—al | 551 | 4 | 0 | 0 | | 1.1 | 0.34 | 100 | 0 | 73 | 77 |

TABLE 3-continued

| Example | Catalyst[a] | Temp. (°C.) | Additives[b] N₂ | H₂ | NH₃ | H₂O | Sup. V. (ft/sec) | Sup. V. (m/sec) | Conv. (%) | Net Yield (%) MePip | Beta | Mat. Bal. (%) |
|---|---|---|---|---|---|---|---|---|---|---|---|---|
| 35A | 9% V2O5 8% ZnO on si—al | 551 | 5 | 0 | 0 | | 1.0 | 0.30 | 100 | 0 | 100 | 89 |
| 36A[c] | 11% CuO-11% Cr2O3 on si—al | 552 | 5 | 0 | 0 | 5.9 | 0.8 | 0.24 | 100 | 0 | 65 | 78 |

[a]Percentages were by weight of total catalyst used as prepared or commercially obtained.
[b]Expressed as moles per mole of organic in feed stream.
[c]Organic feeds were 1:1 weight ratios of "DYTEK-A" and commercial 3-methylpiperidine.

EXAMPLE 37

In this Example, a fixed-bed reactor was used. It comprised a 1-inch (2.5-cm) ID×3-foot (91-cm) 316 stainless steel pipe covered with a sodium-filled jacket, covered in turn with a gas furnace. The catalyst charge was 250 ml (401 g) of Harshaw copper chromite #Cu-1107T as used in Example 1. The form of the catalyst was 0.125-inch (0.32-cm)×0.125-inch (0.32-cm) cylindrical pellets. 24 g of MPDA/hour and 26 g of water/hour were fed from a single-stroke piston pump, vaporized and heated to 240° C. in an electrically heated 0.5-inch (1.3-cm)×1-foot (30-cm) stainless steel pipe and passed downward through the reactor. The reactor temperature was maintained at 552° C. The product was collected by condensation in a coil of tubing submerged in ice water. The combined product from the 1-hour run was analyzed as in Example 1, showing 94% conversion with no MePip and 97% net yield of Beta.

EXAMPLE 38

This reaction was carried out as in Example 2(A) (i) using 760 mL (700 g) of MoO3 on an equilibrium cracking catalyst (containing 6% MoO3) which was prepared in the conventional manner. The organic feed was from the hydrogenation of MGN, comprising a mixture of 42% MePip, 51% MPDA and 7% other organic by-products. Thereafter, a feed of 220 g of the MGN hydrogenation products/hour, 230 g of water/hour and 209 L of nitrogen/hour at a reaction temperature of 550° C. resulted in 99% conversion of the feed with 76% net yield of Beta in the first 30-minute run and 100% conversion of the feed with 83% net yield of Beta in the second 30-minute run. Only traces of MePip were seen in the recovered product from these runs.

What is claimed is:

1. A high temperature process for the selective production of 3-methylpyridine in high yield, comprising the step of:
   contacting a vaporized feed stream containing 2-methyl-1,5-pentanediamine with a metal-oxide catalyst, said contacting being at a temperature of about 500°-600° C. for a time of less than about 30 seconds wherein said catalyst comprises an oxide of:
   molybdenum;
   cadmium;
   copper;
   chromium;
   copper-chromium;
   iron;
   tungsten;
   bismuth;
   cobalt;
   lanthanum;
   niobium;
   zinc;
   silicon;
   aluminum;
   lead;
   antimony;
   thorium;
   titanium;
   vanadium;
   palladium;
   manganese; or
   cesium.

2. The process of claim 1 in which the feed stream also contains 3-methylpiperidine.

3. The process of claim 2 in which the feed stream contains the hydrogenation products of 2-methylglutaronitrile.

4. The process of claim 2 in which said contacting is in a fluid-bed reactor.

5. The process of claim 1 in which the catalyst comprises a metal-oxide of other than a precious metal.

6. The process of claim 1 in which the catalyst comprises an oxide of zinc.

7. The process of claim 6 additionally comprising the steps of:
   separating and recovering the 3-methylpyridine after said contacting.

8. The process of claim 7 in which a reaction product is formed from which said 3-methylpyridine is recovered in a comparative yield of about 3:1 or more relative to 3-methylpiperidine in said reaction product.

9. The process of claim 8 additionally comprising the steps of:
   initially charging a reactor with an amount of the catalyst, said contacting including passing the vaporized feed stream through the charged and heated reactor, said separating and recovering including condensing the product stream exiting the reactor and isolating the 3-methylpyridine product by distillation.

10. The process of claim 9 additionally comprising the steps of:
    isolating 3-methylpiperidine product in the stream exiting the reactor also by distillation and recycling the same to said contacting step.

11. The process of claim 10 wherein said contacting, separating and recovering steps can be repeated with new or recycled feed streams and without regenerating the catalyst while still recovering effective yields of the 3-methylpyridine product.

12. The process of claim 11 additionally comprising repeating runs of said contacting, separating and recovering steps with new or recycled feed streams and without regenerating the catalyst.

13. The process of claim 1 in which the catalyst comprises a metal-oxide selected from the group consisting of copper chromite, molybdenum oxide, and vanadium oxide.

14. The process of claim 13 in which the catalyst comprises copper chromite.

15. The process of claim 13 in which the catalyst comprises molybdenum oxide.

16. The process of claim 13 in which the catalyst comprises vanadium oxide.

17. The process of claim 13 in which the copper chromite, molybdenum oxide, or vanadium oxide is supported on silica, silica-alumina, or alumina.

18. The process of claim 13 in which said contacting is at a temperature of about 550° C.

19. The process of claim 13 in which the feed stream also contains water.

20. The process of claim 19 in which the water is present in a molar ratio of about 5:1 or more water to organic in the feed stream.

21. The process of claim 13 in which the feed stream also contains hydrogen.

22. The process of claim 21 in which the hydrogen is present in a molar ratio of about 1:1 or more hydrogen to organic in the feed stream.

23. The process of claim 13 in which the feed stream also contains ammonia.

24. The process of claim 23 in which the ammonia is present in a molar ratio of about 1:1 or more ammonia to organic in the feed stream.

25. The process of claim 13 in which the feed stream also contains an inert gas.

26. The process of claim 25 in which the inert gas is present in a molar ratio of about 1:1 or more compared to the total of 2-methyl-1,5-pentanediamine and 3-methylpiperidine in the feed stream.

27. The process of claim 13 in which said contacting is for a time less than about 10 seconds.

28. The process of claim 27 in which said recovered 3-methylpyridine product is present in comparative yields of about 10:1 or more relative to 3-methylpiperidine product from said runs.

29. The process of claim 28 in which said 3-methylpyridine product is recovered in an effective yield approaching about 40% or more based on a conversion approaching 100% after said contacting.

* * * * *